United States Patent

Pitterna et al.

(10) Patent No.: US 6,677,457 B2
(45) Date of Patent: Jan. 13, 2004

(54) PROCESS FOR THE PREPARATION OF THIAZOLE DERIVATIVES

(75) Inventors: Thomas Pitterna, Basel (CH); Henry Szczepanski, Wallbach (CH); Peter Maienfisch, Rodersdorf (CH); Ottmar Franz Hüter, Lörrach (DE); Thomas Rapold, Wallbach (CH); Marcel Senn, Blonay (CH); Thomas Göbel, Lörrach (DE); Anthony Cornelius O'Sullivan, Basel (CH); Gottfried Seifert, Magden (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/047,807

(22) Filed: Jan. 15, 2002

(65) Prior Publication Data

US 2003/0065191 A1 Apr. 3, 2003

Related U.S. Application Data

(62) Division of application No. 09/628,392, filed on Aug. 1, 2000, now Pat. No. 6,369,233, which is a division of application No. 09/331,432, filed on Aug. 13, 1999, now Pat. No. 6,121,455.

(30) Foreign Application Priority Data

Dec. 19, 1996 (CH) .................................................. 3124/96

(51) Int. Cl.$^7$ ............................................ C07D 277/16
(52) U.S. Cl. .................................................... 548/182
(58) Field of Search ........................................ 548/182

(56) References Cited

U.S. PATENT DOCUMENTS 5,245,040 A * 9/1993 Maienfisch et al. ......... 546/332

FOREIGN PATENT DOCUMENTS

WO 9723469 3/1997

\* cited by examiner

*Primary Examiner*—Joseph K. McKane
*Assistant Examiner*—Ebenezer Sackey
(74) *Attorney, Agent, or Firm*—Rose M. Allen

(57) ABSTRACT

The invention relates to a process for the preparation of a compound of the formula

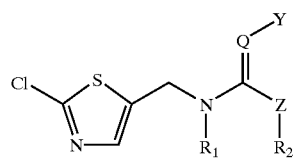
(I)

wherein Q, Y, Z, $R_1$, $R_2$, $R_3$, $R_4$ and $R_5$ are as defined in the specification, which comprises a) reacting a compound of the formula

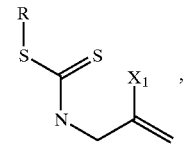
(II)

with a halogenating agent to form a compound of the formula

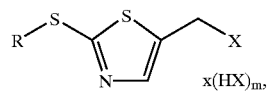
(III)

or b) converting a compound of formula (II) by means of a halogenating agent into a compound of the formula

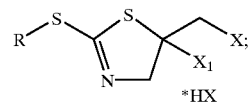
(IV)

optionally c) converting the compound of formula (IV) into a compound of formula (III);

d) converting a compound of formula (III) by means of a compound of the formula

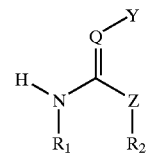
(V)

into a compound of the formula

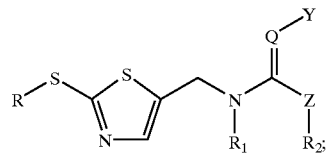
(VI)

or e) converting a compound (IV) by means of a compound (V) into a compound (VI); and f) converting a compound (VI) by means of a chlorinating agent into a compound (I);

a compound (IV); to a process for the preparation of a compound (III) and to a process for the preparation of a compound (IV).

1 Claim, No Drawings

PROCESS FOR THE PREPARATION OF THIAZOLE DERIVATIVES

This appln is a Div of Ser. No. 09/628,392 filed Aug. 1, 2000 now U.S. Pat. No. 6,369,233 which is a Div of Ser. No. 09/331,432 filed Aug. 13, 1999 now U.S. Pat. No. 6,121,455.

The invention relates to a process for the preparation of a compound of the formula

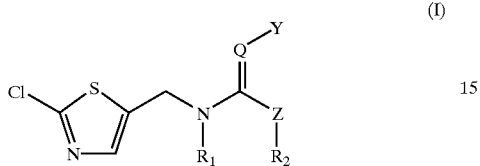

(I)

and, where applicable, its E/Z-isomers, mixtures of E/Z-isomers and/or tautomers, in each case in free form or in salt form, wherein Q is CH or N, Y is $NO_2$ or CN, Z is $CHR_3$, O, $NR_3$ or S, $R_1$ and $R_2$ are either each independently of the other hydrogen or unsubstituted or $R_4$-substituted $C_1$–$C_8$alkyl, or together form an alkylene bridge having two or three carbon atoms, and said alkylene bridge may additionally contain a hetero atom selected from the group consisting of $NR_5$, O and S, $R_3$ is H or unsubstituted or $R_4$-substituted $C_1$–$C_{12}$alkyl, $R_4$ is unsubstituted or substituted aryl or heteroaryl, and $R_5$ is H or $C_1$–$C_{12}$alkyl;

which comprises a) reacting a compound of the formula

(II)

and, where applicable, its E/Z-isomers, mixtures of E/Z-isomers and/or tautomers, in each case in free form or in salt form, which is known or can be prepared by processes known per se and wherein R is unsubstituted or substituted $C_1$–$C_{12}$alkyl, unsubstituted or substituted $C_2$–$C_4$alkenyl, unsubstituted or substituted $C_2$–$C_4$alkynyl, unsubstituted or substituted $C_3$–$C_6$cycloalkyl, unsubstituted or substituted aryl, unsubstituted or substituted heterocyclyl, or –$SR_6$; and $R_6$ is unsubstituted or substituted $C_1$–$C_{12}$alkyl, unsubstituted or substituted $C_2$–$C_4$alkenyl, unsubstituted or substituted $C_2$–$C_4$alkynyl, unsubstituted or substituted $C_3$–$C_6$cycloalkyl, unsubstituted or substituted aryl or unsubstituted or substituted heterocyclyl, $X_1$ is a leaving group;

with a halogenating agent, in the presence of a base, to form a compound of the formula

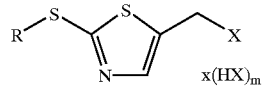

(III)

or, where applicable, an E/Z-isomer, a mixture of E/Z-isomers and/or a tautomer thereof, wherein R is as defined for formula (II);

m is 0 or 1; and

X is halogen; or b) converting a compound of formula (II) by means of a halogenating agent into a compound of the formula

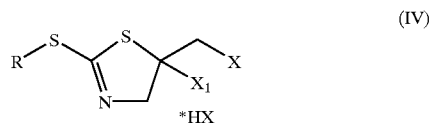

(IV)

or, where applicable, an E/Z-isomer, a mixture of E/Z-isomers and/or a tautomer thereof, wherein R, X and $X_1$ are as defined above for formulae (II) and (III); optionally c) converting a compound of formula (IV), in the absence or in the presence of a base, preferably in the presence of a base, into a compound of formula (III);

d) converting a compound of formula (III) by means of a compound of the formula

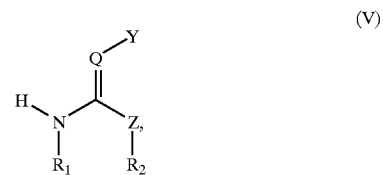

(V)

or, where applicable, an E/Z-isomer, a mixture of E/Z-isomers and/or a tautomer thereof, in each case in free form or in salt form, which is known or can be prepared by processes known per se and wherein $R_1$, $R_2$, Y, Z and Q are as defined above for the compound of formula (I), into a compound of the formula

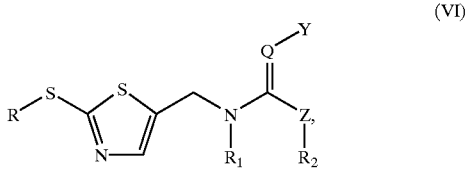

(VI)

or, where applicable, an E/Z-isomer, a mixture of E/Z-isomers and/or a tautomer thereof, in each case in free form or in salt form, which is known or can be prepared by processes known per se and wherein $R_1$, $R_2$, Y, Z and Q are as defined above for the compound of formula (I) and R is as defined above for the compound of formula (II); or e) converting a compound of formula (IV) by reaction with a compound of formula (V) into a compound of formula (VI); and f) converting a compound of formula (VI) by means of a chlorinating agent into a compound of formula (I);

and in each case, if desired, converting a compound of formula (I) obtainable in accordance with the process or by another method, or an E/Z-isomer or tautomer thereof, in each case in free form or in salt form, into a different compound of formula (I) or an E/Z-isomer or tautomer thereof, in each case in free form or in salt form, separating a mixture of E/Z-isomers obtainable in accordance with the process and isolating the desired isomer, and/or converting a free compound of formula (I) obtainable in accordance with the process or by another method, or an E/Z-isomer or tautomer thereof, into a salt or converting a salt, obtainable in accordance with the process or by another method, of a compound of formula (I) or of an E/Z-isomer or tautomer thereof into the free compound of formula (I) or an E/Z-isomer or tautomer thereof or into a different salt.

Methods of synthesis for the compounds of formula (I) are described in the literature. It has been found, however, that the intermediates that have to be used in those synthesis processes known in the literature cause considerable problems during production on account of their high level of toxicity and, moreover, can be removed quantitatively from the active substance only with a significant outlay. Accordingly, the known processes are not satisfactory in that respect, giving rise to the need to make available improved preparation processes for those compounds.

Some compounds of formulae (I), (II), (III), (IV), (V) and (VI) contain asymmetric carbon atoms, as a result of which the compounds may occur in optically active form. Formulae (I) to (VI) are intended to include all those possible isomeric forms as well as mixtures thereof, for example racemates or mixtures of E/Z-isomers.

The general terms used hereinbefore and hereinafter have the meanings given below, unless defined otherwise:

Unless defined otherwise, carbon-containing groups and compounds each contain from 1 up to and including 8, preferably from 1 up to and including 6, especially from 1 up to and including 4, more especially 1 or 2, carbon atoms.

Alkyl—both as a group per se and as a structural element of other groups and compounds, such as haloalkyl, arylalkyl or hydroxyalkyl—is, in each case giving due consideration to the number of carbon atoms contained in the group or compound in question, either straight-chained, i.e. methyl, ethyl, propyl, butyl, pentyl or hexyl, or branched, for example isopropyl, isobutyl, sec-butyl, tert-butyl, isopentyl, neopentyl or isohexyl.

Alkenyl—both as a group per se and as a structural element of other groups and compounds, such as haloalkenyl or arylalkenyl—is, in each case giving due consideration to the number of carbon atoms contained in the group or compound in question, either straight-chained, for example vinyl, 1-methylvinyl, allyl, 1-butenyl or 2-hexenyl, or branched, for example isopropenyl.

Alkynyl—both as a group per se and as a structural element of other groups and compounds, such as haloalkynyl—is, in each case giving due consideration to the number of carbon atoms contained in the group or compound in question, either straight-chained, for example propargyl, 2-butynyl or 5-hexynyl, or branched, for example 2-ethynylpropyl or 2-propargylisopropyl.

$C_3$–$C_8$ Cycloalkyl is cyclopropyl, cyclobutyl, cyclopentyl or cyclohexyl, especially cyclo hexyl.

Aryl is phenyl or naphthyl, especially phenyl.

Heterocyclyl is understood as being a five- to seven-membered monocyclic saturated or unsaturated ring that contains from one to three hetero atoms selected from the group consisting of N, O and S, especially N and S, or a bicyclic ring that may contain either in only one ring—such as, for example, thiazolyl, thiazolinyl, thiazolidinyl, pyrrolyl, pyrrolinyl, pyrrolidinyl, quinolinyl, quinoxalinyl, indolinyl, benzothiophenyl or benzofuranyl—or in both rings—such as, for example, in pteridinyl or purinyl—independently of one another, one or more hetero atoms selected from N, O and S. Preference is given to thiazolyl, thiazolinyl, pyridyl, pyrimidinyl and benzothiazolyl. Heteroaryl is an aromatic mono- or bicyclic ring of the type defined above.

The said heterocyclyl rings are optionally substituted with one to three substituents—according to substitution possibilities on the ring system—selected from the group consisting of halogen, $C_1$–$C_4$alkyl, halogen-$C_1$–$C_4$alkyl and X, wherein X, is as defined hereinbelow. Preferred are chlorine and —$CH_2Cl$.

Halogen—both as a group per se and as a structural element of other groups and compounds, such as haloalkyl, haloalkenyl and haloalkynyl—is fluorine, chlorine, bromine or iodine, especially fluorine, chlorine or bromine, more especially chlorine or bromine, very especially chlorine.

Halo-substituted carbon-containing groups and compounds, such as haloalkyl or haloalkenyl, may be partially halogenated or perhalogenated, the halogen substituents in the case of multi-halogenation being the same or different. Examples of haloalkyl—both as a group per se and as a structural element of other groups and compounds, such as haloalkenyl—are methyl substituted from one to three times by fluorine, chlorine and/or by bromine, such as $CHF_2$ or $CF_3$; ethyl substituted from one to five times by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or by bromine, such as $CH_2CHBrCH_2Br$, $CF_2CHFCF_3$, $CH_2CF_2CF_3$ or $CH(CF_3)_2$; and butyl or an isomer thereof substituted from one to nine times by fluorine, chorine and/or by bromine, such as $CF(CF_3)CHFCF_3$ or $CH_2(CF_2)_2CF_3$. Haloalkenyl is, for example, $CH_2CH=CHCl$, $CH_2CH=CCl_2$, $CH_2CF—CF_2$ or $CH_2CH=CHCH_2Br$.

A leaving group $X_1$ is hereinbefore and hereinafter understood as being all in connection with chemical reactions atoms or groups which can act as leaving groups and which are known to the artisan. Preferred are halogen, such as fluorine, chlorine, bromine and iodine; —O—C(=O)—A, —O—P(=O)(—A)$_2$, —O—Si($C_1$–$C_8$-Alkyl)$_3$, —O—($C_1$–$C_8$-Alkyl), —O—Aryl, —O—S(=O)$_2$A, —S—P(=O)(—A)$_2$, —S—P(=S)(—A)$_2$, —S—S—($C_1$–$C_8$-Alkyl), —S—S-Aryl, —S—($C_1$–$C_8$-Alkyl), —S—Aryl, —S(=O)A, or —S(=O)$_2$A, wherein A is $C_1$–$C_8$-alkyl, $C_2$–$C_8$-alkenyl, $C_2$–$C_8$-alkinyl, aryl or benzyl, which are unsubstituted or substituted; $C_1$–$C_8$-alkoxy or di-($C_1$–$C_8$-alkyl)amin, wherein the alkyl groups are independent of each other; $NO_3$, $NO_2$, sulfate, sulfite, phosphate, phosphite, carboxylate, iminoester, $N_2$ or carbamate. Preferred leaving groups are chlorine and bromine, especially chlorine. Other preferred leaving groups are given in the examples.

Some compounds of formulae (I), (V) and (VI) may be in the form of tautomers. Therefore, hereinbefore and hereinafter the compounds of formulae (I), (V) and (VI) are to be understood as including also the corresponding tautomers, even if the latter are not mentioned specifically in every case.

Compounds of formulae (I), (II), (III), (V) and (VI) that have at least one basic centre are able to form, for example, acid addition salts. These are formed, for example, with strong inorganic acids, such as mineral acids, for example perchloric add, sulfuric acid, nitric acid, nitrous acid, a phosphoric acid or a hydrohalic acid, with strong organic carboxylic acids, such as unsubstituted or substituted, for example halo-substituted, $C_1$–$C_4$alkane-carboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkane- or aryl-sulfonic acids, for example methane- or p-toluene-sulfonic acid. Moreover, compounds of formulae (I), (II), (III), (IV), (V) and (VI) having at least one acid group are able to form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or tri-hydroxy-lower alkylamine, for example mono-, di- or tri-ethanolamine. Furthermore, corresponding internal salts may be formed. Hereinbefore and hereinafter, the compounds of formulae (I) to (VI) are to be understood as being both the compounds of formulae (I) to (VI) in free form and the corresponding salts. The same applies to tautomers of compounds of formulae (I), (V) and (VI) and their salts. In the case of the compounds of formulae (I) to (III), (V) and (VI), preference is in each case generally given to a process for the preparation of the free form.

Within the scope of the invention, preference is given to a process for the preparation of a compound of formula (I) wherein (1) $R_1$ and $R_2$ in the compounds of formulae (I), (V) and (VI) are either each independently of the other hydrogen or $C_1$–$C_4$alkyl, or together form a alkylene bridge containing 2 or 3 carbon atoms, that may additionally contain a hetero atom selected from the group consisting of O and S, or may contain the group $NR_5$, and $R_5$ is H or $C_1$–$C_4$ alkyl; especially, $R_1$ and $R_2$ are each hydrogen or together form a two- or three-membered alkylene bridge that may additionally contain O or $NR_5$, and $R_5$ is $C_1$–$C_4$alkyl;

more especially, $R_1$ and $R_2$ together are —$CH_2$—O—$CH_2$—$CH_2$—$CH_2$—$CH_2$— or —$CH_2$—$CH_2$—;

(2) R in the compounds of the formulae (II), (III), (IV) and (VI) is unsubstituted or substituted $C_1$–$C_{12}$alkyl; unsubstituted or substituted aryl-$C_1$–$C_4$alkyl; unsubstituted or halo-substituted heterocycyl-$C_1$–$C_4$alkyl, aryl-$C_2$–$C_4$alkenyl or heterocycyl-$C_2$–$C_4$alkenyl; unsubstituted or halo-substituted $C_2$–$C_4$alkenyl, $C_2$–$C_4$ alkynyl, aryl -$C_2$–$C_4$alkynyl, heterocycyl-$C_2$–$C_4$alkynyl or $C_4$–$C_6$cycloalkyl; unsubstituted or halo-, $C_1$–$C_4$alkyl-, HO—$C_1$–$C_4$alkyl- or HS—$C_1$–$C_4$alkyl-substituted aryl; unsubstituted or halo- or $C_1$–$C_4$alkyl-substituted heterocycyl; —$CH_2$COO—$C_1$–$C_8$alkyl, —$CH_2$—CO—$C_1$–$C_8$alkyl, $SR_6$, —$(CH_2)_n$—$SR_6$ or —$CH_2$—COO-M, wherein M is hydrogen or a cation and n is from 1 to 8;

especially unsubstituted or halo-, OH— or SH-substituted $C_1$–$C_{12}$alkyl; unsubstituted or halo-substituted aryl-$C_1$–$C_4$alkyl; unsubstituted or halo-substituted heteroaryl-$C_1$–$C_4$alkyl, aryl-$C_1$–$C_4$alkenyl or heteroaryl-$C_1$–$C_4$alkenyl; unsubstituted or halo-substituted $C_2$–$C_4$alkenyl, $C_2$–$C_4$alkynyl, aryl-$C_2$–$C_4$alkynyl, heteroaryl-$C_2$–$C_4$alkynyl or $C_4$–$C_6$cycloalkyl; unsubstituted or halo-, $C_1$–$C_4$alkyl-, HO—$C_1$–$C_4$alkyl- or HS—$C_1$–$C_4$alkyl-substituted aryl; unsubstituted or halo- or $C_1$–$C_4$alkyl-substituted heteroaryl; —$CH_2$—COO—$C_1$–$C_8$alkyl, —$CH_2$—CO—$C_1$–$C_8$alkyl, $SR_6$, —$(CH_2)_n$—$SR_6$ or —$CH_2$—COO-M, wherein M is hydrogen, an alkali metal cation or $(alkyl)_4 N \oplus$ and n is from 1 to 8;

more especially $C_1$–$C_4$alkyl, hydroxy-$C_1$–$C_4$alkyl, $C_3$–$C_4$alkenyl, $C_3$–$C_4$alkynyl, chloro-$C_3$–$C_4$-alkenyl, unsubstituted or chlorine-substituted phenyl, unsubstituted or chlorine-substituted benzyl, heterocyclyl, cyclohexyl, —$CH_2$COO—$C_1$–$C_4$alkyl;

very especially $C_1$–$C_4$alkyl, phenyl, benzyl, cyclohexyl, thiazolyl, benzothiazol-2-yl, —$CH_2$—COO-ethyl or —$CH_2$—COO—Na; especially preferably phenyl or benzyl, most especially phenyl;

(3) R in the compounds of formulae (II), (III), (IV) and (VI) is $SR_6$ or —$(CH_2)_n$—$SR_6$ and $R_6$ is $C_1$–$C_8$alkyl, aryl-$C_1$–$C_4$alkyl, arylthio-$C_1$–$C_4$alkyl, heterocycyl-$C_1$–$C_4$alkyl, heterocycyl-thio-$C_1$–$C_4$alkyl, $C_2$–$C_4$alkenyl, aryl-$C_2$–$C_4$alkenyl, heterocycyl-$C_2$–$C_4$alkenyl, $C_2$–$C_4$alkynyl, aryl-$C_2$–$C_4$alkynyl, heterocycyl-$C_2$–$C_4$alkynyl, cyclohexyl, aryl or heterocycyl;

especially $C_1$–$C_4$alkyl,

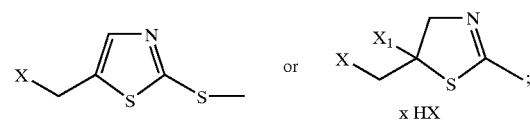

n is 1 or 2, preferably 2; and X and $X_1$ are as defined in the compounds (II) and (III);

(4) X in the compounds of formulae (III) and (IV) is chlorine or bromine.

The reactions of process steps a) to f) described hereinbefore and hereinafter are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately −20° C. to approximately +120° C., especially from 20° C. to 80° C., and, if necessary, in a closed vessel, under pressure, under an inert gas atmosphere and/or under anhydrous conditions. Especially advantageous reaction conditions can be taken from the Examples.

The reactants can in each case be reacted with one another as such, i.e. without the addition of a solvent or diluent, for example in the molten state. However, the addition of an inert solvent or diluent or of a mixture thereof is in most cases advantageous. There may be mentioned as examples of such solvents and diluents:

aromatic, aliphatic and alicyclic hydrocarbons and halogenated hydrocarbons, such as benzene, toluene, xylene, mesitylene, Tetralin, chlorobenzene, dichlorobenzene, bromobenzene, nitrobenzene, nitromethane, petroleum ether, hexane, cyclohexane, dichloromethane, trichloromethane, tetrachloromethane, dichloroethane, trichloroethene or tetrachloroethene; esters, such as ethyl acetate, methyl acetate, dimethyl carbonate, diethyl carbonate, ethoxyethyl acetate, methoxyethyl acetate, ethyl formate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide; or mixtures of such solvents. If the reaction in question is carried out in the presence of a base, bases such as triethylamine, pyridine, N-methylmorpholine or N,N-diethylaniline in excess may also serve as solvent or diluent. Suitable solvents for the reaction in question can be taken from the Examples.

Process Step a)

The reaction is preferably carried out in a temperature range of from −40 to 160° C., especially from −20 to 100° C., customarily from −20 to 25° C.

Solvents that are inert under the prevailing reaction conditions are used, such as aliphatic and aromatic hydrocarbons, halogenated hydrocarbons, lower carboxylic acids, esters, nitriles, amides, ethers; for example: petroleum ether, pentane, hexane, heptane, chlorobenzene, methylene chloride, ethylene chloride, bromochloromethane, chloroform, carbon tetrachloride, tetrachloroethylene, acetic acid, ethyl acetate, acetonitrile, dimethylformamide, dimethylacetamide, diethyl ether, diisopropyl ether, tetrahydrofuran, dioxane; or a mixture thereof; customarily: chlorobenzene, methylene chloride, bromochloromethane, ethyl acetate, acetonitrile, nitrobenzene, nitromethane; or mixtures of such solvents.

Water or a base may be added to the reaction mixture, if desired. Bases for facilitating the reaction are, for example, alkali metal or alkaline earth metal hydroxides, hydrides, amides, alkanolates, acetates, carbonates, dialkylamides or alkylsilylamides; alkylamines, alkylenediamines, free or N-alkylated, saturated or unsaturated cycloalkylamines, basic heterocycles, ammonium hydroxides and also carbocyclic amines. Examples are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and also 1,5-diazabicyclo[5.4.0]-undec-5-ene (DBU). Preferred additives are sodium hydrogen carbonate and water. The procedure generally yields a free compound of formula (III) (m=0). However, the compounds of formula (III) can in many cases also be captured in the form of the hydrohalides, for example for the purpose of simpler isolation. The hydrohalides of formula (III), wherein m is 1, can then be converted into a free compound of formula (III) by the addition of a base or, alternatively, without a base at elevated temperature, preferably at from 40° C. to 140° C.

Suitable halogenating agents are especially chlorine, bromine, iodine, $POCl_3$, $PCl_3$, $PCl_5$, $SO_2Cl_2$ or $SO_2Br_2$, preferably chlorine, bromine or $SO_2Cl_2$.

Process Step b)

The same conditions as under process a) apply in respect of solvents and temperatures; however, the reaction is carried out without the addition of a base.

The reaction is preferably carried out under normal pressure.

The reaction time is not critical; a reaction time of from 0.1 to 24 hours, especially from 0.5 to 6 hours, is preferred.

The product is isolated by the customary methods, for example by means of filtration, crystallisation, distillation or chromatography, or any suitable combination of such methods.

Process Step c)

The solvents and bases used can be taken from the details given with regard to process step a).

The reaction is preferably carried out at a temperature of from approximately 0° C. to approximately +180° C., especially at from approximately +10° C. to approximately +80° C., in many cases at from room temperature to the reflux temperature of the solvent. In an especially preferred form of variant c), a compound of formula (IV) is reacted at from 0° C. to 120° C., especially from 20° C. to 80° C., preferably from 30° C. to 60° C., in an ester, especially in dimethyl carbonate, and preferably in the presence of a base, especially $K_2CO_3$.

The reaction is preferably carried out under normal pressure.

The reaction time is not critical; a reaction time of from 0.1 to 48 hours, especially from 0.5 to 12 hours, is preferred.

The product is isolated by the customary methods, for example by means of filtration, crystallisation, distillation or chromatography, or any suitable combination of such methods.

Process Step d) and e)

Bases are customarily used to facilitate the reaction; they are of the same type as those mentioned under process step a).

The reactants can be reacted with one another as such, i.e. without a solvent or diluent, for example in the molten state. However, the addition of a solvent or diluent is in most cases advantageous. Examples of such solvents and diluents are: water; aromatic, aliphatic and alicyclic hydrocarbons and halogenated hydrocarbons, for example benzene, toluene, xylene, mesitylene, Tetralin, chlorobenzene, dichlorobenzene, bromobenzene, petroleum ether, hexane, cyclohexane, dichloromethane, trichloromethane, carbon tetrachloride, dichloroethane, trichloroethene or tetrachloroethene; esters, such as ethyl acetate, methyl acetate, dimethyl carbonate, diethyl carbonate, methyl formate, ethyl formate, ethoxyethyl acetate, methoxyethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone, methyl isopropyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide; or mixtures of such solvents. If the reaction is carried out in the presence of a base, bases such as triethylamine, pyridine, N-methylmorpholine or N,N-diethylaniline in excess may serve as solvent or diluent.

The reaction may alternatively be carried out in a heterogeneous two-phase mixture, for example a mixture of organic solvents or an organic solvent and an aqueous phase, if necessary in the presence of a phase-transfer catalyst, for example a crown ether or a tetraalkylammonium salt.

In a preferred embodiment of variant d), the reaction is carried out at a temperature between 0° C. to about +180° C., especially between +10° C. and +80° C., in may cases between ambient temperature and the refluxing temperature of the solvent. In a especially preferred embodiment of variant d), the compound of the formula (III) is reacted with a compound of the formula (V) at between 0° C. and 120° C., especially between 20° C. and 80° C., preferably between 60° C. and 80° C., in an amide, preferably N,N-dimethyl-formamide, preferably in the presence of a base, especially $K_2CO_3$.

The reaction is preferably carried out under normal pressure.

The reaction time is not critical; a reaction time of from 0.1 to 48 hours, especially from 0.5 to 12 hours, more especially from 3 to 12 hours, is preferred.

The product is isolated by the customary methods, for example by means of filtration, crystallisation, distillation or chromatography, or any suitable combination of such methods.

The yields achieved are customarily good. A yield of 80% of the theoretical value can often be obtained.

Preferred conditions under which the reaction is carried out can be taken from the Examples.

For process step e) the same process conditions as under variant d) apply, however, an additional equivalent of a base of the type indicated under process step a) is added to the reaction mixture; preferably, at least three molar equivalents of base are added.

In a preferred embodiment of variant e), a compound of the formula (IV) is reacted with a compound of the formula (V), at a temperature between 0° C. and 120° C., especially between 20° C. and 80° C., preferably between 30° C. and 60° C., in a ketone, preferably methylethylketon, preferred in the presence of a base, especially $K_2CO_3$, preferably in the presence of a phase transfer catalyst, especially 1-(chloromethyl)4-aza-1-azoniabicyclo[2.2.2] octanechloride. In another preferred embodiment of variant e) a compound of the formula (IV) is reacted with a compound of the formula (V) at between 0° C. and 120° C., preferably 20° C. and 80° C., especially preferred between 30° C. and 60° C., in an ester, especially dimethylcarbonate, preferably in the presence of a base, especially $K_2CO_3$.

Process Step f)

Suitable halogenating agents are, for example, elementary chlorine, Javelle water, polysulfur dichloride, sulfur dichloride, phosphorus trichloride, phosphorus pentachloride, or mixtures of two or more of those reagents; especially elementary chlorine, Javelle water, sulfur dichloride or a mixture of those compounds, more especially Javelle water.

The reactants can be reacted with one another as such, i.e. without a solvent or diluent, for example in the molten state. However, the addition of a solvent or diluent is in most cases advantageous. Examples of such solvents and diluents are: water; acids such as, for example, hydrochloric acid, sulfuric acid, formic acid or acetic acid; aromatic, aliphatic and alicyclic hydrocarbons and halogenated hydrocarbons, for example benzene, toluene, xylene, mesitylene, Tetralin, chlorobenzene, dichlorobenzene, bromobenzene, petroleum ether, hexane, cyclohexane, dichloromethane, trichloromethane, carbon tetrachloride, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide; or mixtures of such solvents. In a preferred form, the reaction is carried out in a halogenated hydrocarbon, especially in dichloromethane. In an especially preferred form, the reaction is carried out in an aqueous acid, for example hydrochloric acid.

The reaction is preferably carried out at a temperature of from approximately 0° C. to approximately +180° C., especially at from approximately +10° C. to approximately +80° C., in many cases at from room temperature to the reflux temperature of the solvent. In a preferred form of variant f), the reaction is carried out at from 0° C. to 120° C., especially at from 10° C. to 50° C., preferably in aqueous hydrochloric acid.

The reaction is preferably carried out under normal pressure.

The reaction time is not critical; a reaction time of from 0.1 to 48 hours, especially from 2 to 12 hours, is preferred.

The product is isolated by the customary methods, for example by means of filtration, crystallisation, distillation or chromatography, or any suitable combination of such methods.

The yields achieved are customarily good. A yield of 50% of the theoretical value or above can often be obtained.

Preferred conditions under which the reaction is carried out can be taken from the Examples.

Salts of compounds of formulae (I) to (VI) can be prepared in a manner known per se. For example, acid addition salts are obtained by treatment with a suitable acid or a suitable ion exchange reagent, and salts with bases are obtained by treatment with a suitable base or a suitable ion exchange reagent.

Salts of compounds of formulae (I) to (VI) can be converted into the free compounds of formulae (I) to (VI) in customary manner; acid addition salts, for example, by treatment with a suitable basic agent or a suitable ion exchange reagent, and salts with bases, for example, by treatment with a suitable acid or a suitable ion exchange reagent.

Salts of compounds of formulae (I) to (VI) can be converted into different salts of compounds of formulae (I) to (VI) in a manner known per se; acid addition salts, for example, can be converted into different acid addition salts, for example by treating a salt of an inorganic acid, such as a hydrochloride, with a suitable metal salt, such as a sodium, barium or silver salt, of an acid, for example silver acetate, in a suitable solvent in which an inorganic salt that forms, for example silver chloride, is insoluble and therefore separates out of the reaction mixture.

Depending on the procedure and the reaction conditions, the compounds of formulae (I) to (VI) having salt-forming properties can be obtained in free form or in the form of salts.

The compounds of formulae (I) to (VI) and in each case, where applicable, their tautomers, in each case in free form or in salt form, may be in the form of one of the possible isomers or in the form of a mixture thereof, for example, depending on the number of asymmetric carbon atoms occurring in the molecule and their absolute and relative configuration, and/or depending on the configuration of non-aromatic double bonds occurring in the molecule, in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and is to be interpreted as such hereinbefore and hereinafter, even if stereochemical details are not mentioned specifically in every case.

Mixtures of diastereoisomers and mixtures of racemates of compounds of formulae (I) to (VI) which may be obtained by the process according to the starting materials and procedures chosen, or which are obtainable by another method, or their salts, can be separated into the pure diastereoisomers or racemates in known manner on the basis of the physicochemical differences between the constituents, for example by means of fractional crystallisation, distillation and/or chromatography.

Mixtures of enantiomers, such as racemates, that are obtainable in a corresponding manner can be resolved into the optical antipodes by known methods, for example by recrystallisation from an optically active solvent, by chromatography on chiral adsorbents, for example high pressure liquid chromatography (HPLC) on acetylcellulose, with the aid of suitable microorganisms, by cleavage with specific, immobilised enzymes, via the formation of inclusion compounds, for example using chiral crown ethers, only one enantiomer being complexed, or by conversion into diastereoisomeric salts, for example by reacting a basic end-product racemate with an optically active acid, such as a carboxylic acid, for example camphoric, tartaric or malic acid, or a sulfonic acid, for example camphorsulfonic acid, and separating the mixture of diastereoisomers so obtained, for example on the basis of their different solubilities by fractional crystallisation, into the diastereoisomers, from which the desired enantiomer can be freed by the action of suitable, for example basic, agents.

Apart from by separation of corresponding mixtures of isomers, pure diastereoisomers and enantiomers can be obtained according to the invention also by generally known methods of diastereoselective and enantioselective synthesis, for example by carrying out the process according to the invention using starting materials having correspondingly suitable stereochemistry.

The compounds of formulae (I) to (VI) and their salts can also be obtained in the form of their hydrates and/or include other solvents, for example solvents that may have been used for the crystallisation of compounds that occur in solid form.

The invention relates to all those forms of the process according to which a compound obtainable as starting material or intermediate at any stage of the process is used as starting material and all or some of the remaining steps are carried out, or a starting material is used in the form of a derivative or salt and/or in the form of its racemates or antipodes or, especially, is formed under the reaction conditions.

Compounds of formulae (I), (III), (IV), (V) and (VI) obtainable in accordance with the process or by another method can be converted into different corresponding compounds in a manner known per se.

In the process of the present invention there are preferably used those starting materials and intermediates, in each case in free form or in salt form, which lead to the compounds of formulae (I) to (VI) described at the beginning as being especially valuable, or their salts.

The invention relates especially to the preparation processes described in Examples P1 to P4.

The present invention relates also to the compounds of formula (IV) and, where applicable, their E/Z-isomers, mixtures of E/Z-isomers and/or tautomers, in each case in free form or in salt form, wherein R is as defined above for formula (I).

The present invention relates also to processes a) for the preparation of a compound of formula (III) from a compound of formula (II);

b) for the preparation of a compound of formula (IV) from a compound of formula (II);

c) for the preparation of a compound of formula (III) from a compound of formula (IV); and e) for the preparation of a compound of formula (VI) from a compound of formula (IV) and a compound of formula (V), and f) for the preparation of a compound of formula (VI) from a compound of formula (III) and a compound of formula (V).

For substituents R in the compounds of formulae (II), (III), (IV) and (VI), the same preferred meanings as mentioned above in the processes for the preparation of the compounds of formula (I) apply.

The compounds of formulae (I), (II), (III), (V) and (VI) are known, for example as intermediates in the preparation of pesticides, or they can be prepared in accordance with processes known per se.

PREPARATION EXAMPLES

Example P-A (2-Chloro-allyl)-dithiocarbamic acid benzyl ester 47 g of 2-chloro-allyl isothiocyanate and 40 g of benzyl mercaptan are dissolved in 150 ml of acetonitrile and 150 ml of toluene. Then 1 g of 1,4-diazabicyclo[2.2.2]octane is added and the mixture is heated to 75° C. and stirred for one hour. After cooling to room temperature, the solvent is removed by evaporation and the residue is crystallised from ether/hexane. In that manner the title product having a melting point of 46–48° C. (compound A) is obtained.

Example P-B

The other compounds listed in Table 1a can also be prepared in a manner analogous to that described in Example P-A.

TABLE 1a

Compounds of the formula $$\text{R—CH}_2\text{—S(=S)—N(H)—CH}_2\text{—C(=CH}_2\text{)—X}_1 \tag{II}$$

| Comp. No. | R | X₁ | Physical data |
|---|---|---|---|
| A | benzyl | Cl | m.p.: 46–48° C. |
| B | phenyl | Cl | m.p.: 40° C. |
| C | cyclohexyl | Cl | m.p.: 37° C. |
| D | [2-chloroallyl-NH-C(=S)-S-CH₂-CH₂-] | Cl | m.p.: 97–98° C. |
| E | CH₂=CH—CH₂— | Cl | |
| F | ClCH=CH—CH₂— | Cl | |
| G | CH₂=C(CH₃)—CH₂— | Cl | |
| H | CH₂=CH—CH₂—CH₂— | Cl | |
| I | 2-chlorobenzyl | Cl | |
| J | 4-chlorobenzyl | Cl | |
| K | CH≡C—CH₂— | Cl | |
| L | isopropyl | Cl | |
| M | C₂H₅—OC(=O)—CH₂— | Cl | |
| N | 2-methylbenzothiazolyl | Cl | |
| O | n-C₃H₇— | Cl | |
| P | HO—CH₂—CH₂— | Cl | |
| Q | tert-butyl | Cl | |
| R | n-C₁₂H₂₅— | Cl | |
| S | 2-ethyl-pentyl | Cl | |
| T | benzyl | Br | |
| U | phenyl | Br | |
| V | cyclohexyl | Br | |
| W | [2-chloroallyl-NH-C(=S)-S-CH₂-CH₂-] | Br | |
| X | CH₂=CH—CH₂— | Br | |
| Y | ClCH=CH—CH₂— | Br | |
| Z | CH₂=C(CH₃)—CH₂— | Br | |
| AA | CH₂=CH—CH₂—CH₂— | Br | |
| BB | 2-chlorobenzyl | Br | |
| CC | 4-chlorobenzyl | Br | |
| DD | CH≡C—CH₂— | Br | |
| EE | isopropyl | Br | |
| FF | C₂H₅—OC(=O)—CH₂— | Br | |
| GG | 2-methylbenzothiazolyl | Br | |
| HH | n-C₃H₇— | Br | |
| II | HO—CH₂—CH₂— | Br | |
| JJ | tert-butyl | Br | |

TABLE 1a-continued

Compounds of the formula (II)

$$R-CH_2-S-S(=S)-N-CH_2-C(X_1)=CH_2$$

| Comp. No. | R | X₁ | Physical data |
|---|---|---|---|
| KK | n-C₁₂H₂₅— | Br | |
| LL | 2-ethyl-pentyl | Br | |
| MM | benzyl | I | |
| NN | phenyl | I | |
| OO | cyclohexyl | I | |
| PP | CH₂=C(Cl)-CH₂-NH-C(=S)-S-CH₂-CH₂— | I | |
| QQ | benzyl | F | |
| RR | phenyl | F | |
| SS | cyclohexyl | F | |
| TT | CH₂=C(Cl)-CH₂-NH-C(=S)-S-CH₂-CH₂— | F | |
| UU | benzyl | O—SO₂—CF₃ | |
| VV | phenyl | O—SO₂—CF₃ | |
| WW | cyclohexyl | S(=O)₂C₆H₅ | |
| XX | CH₂=C(Cl)-CH₂-NH-C(=S)-S-CH₂-CH₂— | S(=O)₂C₆H₅ | |

Example P1a
2-Benzylsufanyl-5-chloromethyl-thiazole

Under a slight stream of nitrogen, 35.8 g of (2-chloro-allyl)-dithiocarbamic acid benzyl ester and 31.8 g of sodium hydrogen carbonate are placed in 250 ml of chlorobenzene. The mixture is then cooled to 5–6° C. The apparatus is flushed thoroughly with nitrogen. Then 28.2 g of sulfuryl chloride are added in the course of 120 minutes in such a manner that the temperature can be maintained at 5–10° C. When the addition is complete, stirring is carried out for about 20 minutes. The reaction mixture is filtered off with suction, the filtration residue is washed with 20 ml of chlorobenzene, and the filtrate is thoroughly degassed in vacuo at 20–25° C. Then the solvent is removed by distillation at 30° C. under reduced pressure. 90 ml of hexane are added to the residue. Seeding is carried out, then the mixture is stirred at about 0° C. and about 0.8 g of hydrogen chloride gas is introduced until the solution will take up no more gas. The mixture is stirred for a further 15 minutes, the crude product is filtered off at 0–5° C., and the filtration residue is washed with 10 ml of hexane and dried in vacuo. In that manner 2-benzylsulfanyl-5-chloromethyl-thiazole is obtained in the form of the hydrochloride.

Example P1b
2-Benzylsulfanyl-5-chloromethyl-thiazole 5.0 g of (2-chloro-allyl)-dithiocarbamic acid benzyl ester and 4.1 g of sodium hydrogen carbonate are placed in 100 ml of dichloromethane and cooled in an ice bath. In the course of 3 minutes, a solution of 3.2 g of sulfuryl chloride in 10 ml of dichloromethane is added, and when the addition is complete the ice bath is removed. The mixture is stirred at room temperature for 2 hours and filtered off with suction, and the filtrate is concentrated by evaporation. The residue crystallises after the addition of diethyl ether. Filtration yields 2-benzylsulfanyl-5-chloromethyl-thiazole having a melting point of 129–131° C. in the form of the hydrochloride. Extraction of the mother liquor with semi-saturated aqueous sodium hydrogen carbonate solution and removal of the ether by distillation yield 2-benzylsulfanyl-5-chloromethyl-thiazole having a melting point of 57–61° C.

Example P1c

The other compounds listed in Table 1b can also be prepared in a manner analogous to that described in Examples P1a and P1b.

TABLE 1b

Compounds of the formula

R-S-[thiazole]-CH2-X  x(HX)m

| Comp. No. | R | X | (HX)m | Physical data |
|---|---|---|---|---|
| 1.1 | benzyl | Cl | — | m.p.: 57–59° C. |
| 1.2 | benzyl | Cl | HCl | m.p.: 131° C. (decomp.) |
| 1.3 | benzyl | Br | — | |
| 1.4 | benzyl | Br | HBr | |
| 1.5 | phenyl | Cl | — | |
| 1.6 | phenyl | Cl | HCl | |
| 1.7 | phenyl | Br | — | |
| 1.8 | phenyl | Br | HBr | |
| 1.9 | cyclohexyl | Br | — | |
| 1.10 | cyclohexyl | Br | HBr | |
| 1.11 | ClCH2-[thiazole]-S-(CH2)2- | Cl | — | |
| 1.12 | $CH_2=CH-CH_2-$ | Cl | — | |
| 1.13 | $ClCH=CH-CH_2-$ | Cl | — | |
| 1.14 | $CH_2=C(CH_3)-CH_2-$ | Cl | — | |
| 1.15 | $CH_2=CH-CH_2-CH_2-$ | Cl | — | |
| 1.16 | 2-chlorobenzyl | Cl | — | |
| 1.17 | 4-chlorobenzyl | Cl | — | |
| 1.18 | $CH\equiv C-CH_2-$ | Cl | — | |
| 1.19 | isopropyl | Cl | — | |
| 1.20 | $C_2H_5-OC(=O)-CH_2-$ | Cl | — | |
| 1.21 | 2-benzothiazolyl | Cl | — | |
| 1.22 | $n-C_3H_7-$ | Cl | — | |
| 1.23 | $HO-CH_2-CH_2-$ | Cl | — | |
| 1.24 | tert-butyl | Cl | — | |
| 1.25 | $n-C_{12}H_{25}-$ | Cl | — | |
| 1.26 | 2-ethyl-pentyl | Cl | — | |
| 1.27 | isopropyl | Br | — | |
| 1.28 | $C_2H_5-OC(=O)-CH_2-$ | Br | — | |
| 1.29 | 2-benzothiazolyl | Br | — | |
| 1.30 | $n-C_3H_7-$ | Br | — | |
| 1.31 | $HO-CH_2-CH_2-$ | Br | — | |
| 1.32 | tert-butyl | Br | — | |
| 1.33 | $n-C_{12}H_{25}-$ | Br | — | |
| 1.34 | 2-ethyl-pentyl | Br | — | |

Example P2a 1,2-Bis(5'-bromomethyl-5'-chloro-4,5-dihydro-thiazol-2'-yl-mercapto)-ethane dihydrobromide 100 g of acetonitrile are placed in a reactor. At 10–20° C., with stirring, a solution of 36 g of (2-chloro-allyl)-dithiocarbamic acid 2-(2-chloro-allylthio-carbamoyl-sulfanyl)-ethyl ester in 100 g of acetonitrile and 34 g of bromine are metered in simultaneously within a period of 30 minutes. When the metering in is complete, stirring is continued for a further 30 minutes at 20° C. The product is isolated by filtration over a glass frit, washed with 50 g of acetonitrile and dried in vacuo at 30° C. The title product is obtained in the form of the dihydrobromide (compound 2.4).

Example P2b

2-Benzylsulfanyl-5-bromomethyl-5-chloro-4,5-dihydro-thiazole hydrobromide

Under a slight stream of nitrogen, 19.9 g of (2-chloro-allyl)-dithiocarbamic acid benzyl ester are placed in 100 ml of ethyl acetate and cooled to 0–1° C. During the addition of bromine, the apparatus is flushed thoroughly with nitrogen. 14.0 g of bromine are added in the course of 40 minutes in such a manner that the temperature can be maintained at 0–10° C. When the addition is complete, stirring is carried out for about 20 minutes. The reaction mixture is concentrated in vacuo at 20–25° C. 50 ml of hexane are added, the mixture is filtered at 20–25° C., and the filtration residue is washed with 40 ml of hexane and dried in vacuo at room temperature. The title product is obtained in the form of the hydrobromide (compound 2.1).

Example P2c
5-Bromomethyl-5-chloro-2-phenylsulfanyl-4,5-dihydrothiazole hydrobromide Under a slight stream of nitrogen, 18.4 g of (2-chloroallyl)-dithiocarbamic acid phenyl ester are placed in 100 ml of bromochloromethane and cooled to 0–1° C. Before and during the addition of bromine, the apparatus is flushed thoroughly with nitrogen. 13.8 g of bromine are added in the course of 120 minutes in such a manner that the temperature can be maintained at 0–10° C. When the addition is complete, stirring is carried out for about 20 minutes. The reaction mixture is concentrated in vacuo at 20–25° C. 50 ml of hexane are added to the residue, and the product is filtered off with suction at 20–25° C., washed with 30 ml of hexane and dried in vacuo at room temperature. The title product is obtained in the form of the hydrobromide (compound 2.2).

Analysis: C 29.9%, N 3.6%, Cl 8.9%, S 15.8%, Br 39.1% (calc.: C 28.7%, N 3.5%, S 15.8%, Cl 8.8%, Br 38.5%)

Example P2d
5Bromomethyl-5-chloro-2-cyclohexylsulfanyl-4,5-dihydrothiazole hydrobromide Under a slight stream of nitrogen, 19.0 g of (2-chloroallyl)-dithiocarbamic acid cyclohexyl ester are placed in 100 ml of acetonitrile and cooled to 0–1° C. Before and during the addition of bromine, the apparatus is flushed thoroughly with nitrogen. Then 14.0 g of bromine are added in the course of 70 minutes in such a manner that the temperature can be maintained at 0–10° C. When the addition is complete, stirring is carried out for about 20 minutes. The reaction mixture is concentrated in vacuo at 20–25° C. 50 ml of hexane are added to the crude product, and the product is filtered off with suction at 20–25° C., washed twice with 45 ml of hexane and dried in vacuo at room temperature. The title product is obtained in the form of the hydrobromide (compound 2.3).

Example P2e

The other compounds listed in Table 2 can also be prepared in a manner analogous to that described in Examples P2a to P2d.

TABLE 2

Compounds of the formula

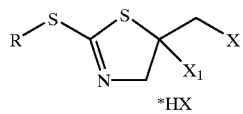

(IV)

*HX

| Comp. No. | R | X | $X_1$ | Physical data |
|---|---|---|---|---|
| 2.1 | benzyl | Br | Cl | m.p.: 95–96° C. |
| 2.2 | phenyl | Br | Cl | m.p.: 122° C. (decomp.) |
| 2.3 | cyclohexyl | Br | Cl | m.p.: 93–115° C. (decomp.) |
| 2.4 | ![structure with Cl, Br, N, S, *HBr, S—CH₂—CH₂—] | Br | Cl | m.p.: 175° C. (decomp.) |
| 2.5 | benzyl | Br | Br | |
| 2.6 | phenyl | Br | Br | |
| 2.7 | cyclohexyl | Br | Br | |
| 2.8 | ![structure with Cl, Br, N, S, *HBr, S—CH₂—CH₂—] | Br | Br | |
| 2.9 | benzyl | Br | I | |
| 2.10 | phenyl | Br | I | |
| 2.11 | benzyl | Br | F | |
| 2.12 | phenyl | Br | F | |
| 2.13 | $CH_2$=CH—$CH_2$— | Br | Cl | |
| 2.14 | ClCH=CH—$CH_2$— | Br | Cl | |
| 2.15 | $CH_2$=C($CH_3$)—$CH_2$— | Br | Cl | |
| 2.16 | $CH_2$=CH—$CH_2$—$CH_2$— | Br | Cl | |
| 2.17 | 2-chlorobenzyl | Br | Cl | |
| 2.18 | 4-chlorobenzyl | Br | Cl | |
| 2.19 | CH≡C—$CH_2$— | Br | Cl | |
| 2.20 | isopropyl | Br | Cl | |
| 2.21 | $C_2H_5$—OC(=O)—$CH_2$— | Br | Cl | |
| 2.22 | 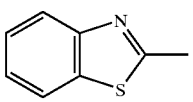 | Br | Cl | |

TABLE 2-continued

Compounds of the formula

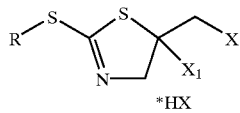

(IV)

*HX

| Comp. No. | R | X | X$_1$ | Physical data |
|---|---|---|---|---|
| 2.23 | n-C$_3$H$_7$— | Br | Cl | |
| 2.24 | HO—CH$_2$—CH$_2$— | Br | Cl | |
| 2.25 | tert-butyl | Br | Cl | |
| 2.26 | n-C$_{12}$H$_{25}$— | Br | Cl | |
| 2.27 | 2-ethyl-pentyl | Cl | Cl | |
| 2.28 | benzyl | Cl | Cl | |
| 2.29 | phenyl | Cl | Cl | |
| 2.30 | cyclohexyl | Cl | Cl | |
| 2.31 | ![structure with Cl, Br, *HBr, S—CH$_2$—CH$_2$—] | Cl | Cl | |
| 2.32 | benzyl | Cl | Br | |
| 2.33 | phenyl | Cl | Br | |
| 2.34 | cyclohexyl | Cl | Br | |
| 2.35 | ![structure with Cl, Br, *HBr, S—CH$_2$—CH$_2$—] | Cl | Br | |
| 2.36 | benzyl | Cl | I | |
| 2.37 | phenyl | Cl | I | |
| 2.38 | benzyl | Cl | F | |
| 2.39 | phenyl | Cl | F | |
| 2.40 | CH$_2$=CH—CH$_2$— | Cl | Cl | |
| 2.41 | ClCH=CH—CH$_2$— | Cl | Cl | |
| 2.42 | CH$_2$=C(CH$_3$)—CH$_2$— | Cl | Cl | |
| 2.43 | CH$_2$=CH—CH$_2$—CH$_2$— | Cl | Cl | |
| 2.44 | 2-chlorobenzyl | Cl | Cl | |
| 2.45 | 4-chlorobenzyl | Cl | Cl | |
| 2.46 | CH≡C—CH$_2$— | Cl | Cl | |
| 2.47 | isopropyl | Cl | Cl | |
| 2.48 | C$_2$H$_5$—OC(=O)—CH$_2$— | Cl | Cl | |
| 2.49 | ![2-benzothiazolyl structure] | Cl | Cl | |
| 2.50 | n-C$_3$H$_7$— | Cl | Cl | |
| 2.51 | HO—CH$_2$—CH$_2$— | Cl | Cl | |
| 2.52 | tert-butyl | Cl | Cl | |
| 2.53 | n-C$_{12}$H$_{25}$— | Cl | Cl | |
| 2.54 | 2-ethylpentyl | Cl | Cl | |

Example P3a
(2-Phenylthio-thiazol-5-yl-methyl)-5-methyl-4-nitroimino-perhydro-1,3,5-oxadiazine 17.6 g of 3-methyl-4-nitroimino-perhydro-1,3,5-oxadiazine, 0.1 g of 1-(chloromethyl)-4-aza-1-azoniabicyclo[2.2.2]octane chloride and 48.3 g of powdered potassium carbonate are placed in 100 g of methyl ethyl ketone. At from 35 to 40° C., 40.4 g of 5-bromomethyl-5-chloro-2-phenylsulfanyl-4,5-dihydro-thiazole hydrobromide are introduced in the form of a powder over a period of 2 hours. After 4 hours, 120 ml of water are added to the reaction mixture, the pH is adjusted to 6 with concentrated hydrochloric acid, the mixture is heated to 70° C. and the aqueous phase is separated off. The organic phase is concentrated to half the volume and cooled to 0° C., and the solid product is filtered off, washed with 10 ml of cold methyl ethyl ketone and dried in vacuo at 50° C. The title product having a melting point of 147° C is obtained (compound 3–2.3).

Example P3b
3-(2-Phenylthio-thiazol-5-yl-methyl)-5-methyl-4-nitroimino-perhydro-1,3,5-oxadiazine 17.6 g of 3-methyl-4-nitroimino-perhydro-1,3,5-oxadiazine, 0.1 g of 1-(chloromethyl)-4-aza-1-azoniabicyclo[2.2.2]octane chloride and 48.3 g of powdered potassium carbonate are placed in 100 g of dimethyl carbonate. At from 35 to 40° C., 40.4 g of 5-bromomethyl-5-chloro-2-phenylsulfanyl-4,5-dihydro-thiazole hydrobromide are introduced in the form of a powder over a period of 2 hours. After 4 hours, 120 ml of water are added to the reaction mixture, the pH is adjusted to 6 with concentrated hydrochloric acid, and the mixture is heated to 70° C. The product dissolves in the organic phase and is separated from the aqueous phase. The organic phase is concentrated to half the volume and cooled to 0° C., and the solid product is filtered off, washed with 10 ml of cold methyl ethyl ketone and dried in vacuo at 50° C. The title product having a melting point of 147° C. is obtained (compound 3–2.3).

Example P3c
3-(2-Cyclohexylthio-thiazol-5-yl-methyl)-5-methyl-4-nitroimino-perhydro-1,3,5-oxadiazine 17.6 g of 3-methyl-4-nitroimino-perhydro-1,3,5-oxadiazine and 41.5 g of powdered potassium carbonate are placed in 100 g of methyl ethyl ketone. At from 30 to 35° C., 36.7 g of 5-bromomethyl-5-chloro-2-cyclohexylsulfanyl-4,5-dihydro-thiazole hydrobromide are introduced in the form of a powder over a period of 2 hours. After 4 hours, 120 ml of water are added to the reaction mixture, the pH is adjusted to 6 with concentrated hydrochloric acid, and the mixture is heated to 70° C. The product dissolves in the organic phase and is separated from the aqueous phase. The organic phase is cooled to 0° C. and the solid product is filtered off, washed with 10 ml of cold methyl ethyl ketone and dried in vacuo at 50° C. The title product having a melting point of 109–110° C. is obtained (compound 3–2.10).

Example P3d

The other compounds listed in Tables 3-1 and 3-2 can also be prepared in a manner analogous to that described in Examples P3a to P3c.

TABLE 3-1

Compounds of the formula

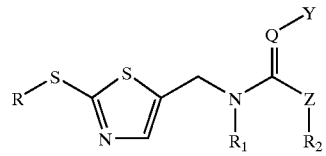

| Comp. No. | R | $R_1$ | $Z-R_2$ | Q-Y | M.p. (° C.) |
|---|---|---|---|---|---|
| 3-1.1 | benzyl | H | $NH_2$ | $CHNO_2$ | |
| 3-1.2 | benzyl | $CH_3$ | $NH_2$ | $CHNO_2$ | |
| 3-1.3 | benzyl | $C_2H_5$ | $NH_2$ | $CHNO_2$ | |
| 3-1.4 | benzyl | $C_2H_5$ | $NHCH_3$ | $CHNO_2$ | |
| 3-1.5 | benzyl | H | $NHCH_3$ | $N-NO_2$ | |
| 3-1.6 | benzyl | H | $NHC_2H_5$ | $N-NO_2$ | |
| 3-1.7 | benzyl | $CH_3$ | $NHCH_3$ | $N-NO_2$ | |
| 3-1.8 | benzyl | H | $NHCH_3$ | $N-NO_2$ | |
| 3-1.9 | benzyl | $CH_3$ | $NH_2$ | $N-NO_2$ | |
| 3-1.10 | benzyl | H | $NH_2$ | $N-NO_2$ | |
| 3-1.11 | benzyl | $CH_3$ | $NH-n-C_3H_7$ | $N-NO_2$ | |
| 3-1.12 | phenyl | H | $NHCH_3$ | $N-NO_2$ | |
| 3-1.13 | phenyl | H | $NHC_2H_5$ | $N-NO_2$ | |
| 3-1.14 | phenyl | $CH_3$ | $NHCH_3$ | $N-NO_2$ | |
| 3-1.15 | phenyl | H | $NHCH_3$ | $N-NO_2$ | |
| 3-1.16 | phenyl | $CH_3$ | $NH_2$ | $N-NO_2$ | |
| 3-1.17 | phenyl | H | $NH_2$ | $N-NO_2$ | |
| 3-1.18 | phenyl | $CH_3$ | $NH-n-C_3H_7$ | $N-NO_2$ | |
| 3-1.19 | phenyl | $CH_3$ | NH-tert-butyl | $N-NO_2$ | |
| 3-1.20 | phenyl | $CH_3$ | NH-n-butyl | $N-NO_2$ | |
| 3-1.21 | phenyl | H | $N(CH_3)_2$ | $N-NO_2$ | |
| 3-1.22 | phenyl | $CH_3$ | $N(CH_3)_2$ | $N-NO_2$ | |
| 3-1.23 | benzyl | H | $NH_2$ | $N-CN$ | |
| 3-1.24 | phenyl | H | $NHC_2H_5$ | $N-NO_2$ | |
| 3-1.25 | phenyl | $CH_3$ | $NHCH_3$ | $N-CN$ | |
| 3-1.26 | phenyl | $CH_3$ | $N(CH_3)_2$ | $CHNO_2$ | |
| 3-1.27 | phenyl | $CH_3$ | $NHC_2H_5$ | $CHNO_2$ | |
| 3-1.28 | cyclohexyl | $CH_3$ | $NH_2$ | $CHNO_2$ | |
| 3-1.29 | cyclohexyl | $C_2H_5$ | $NH_2$ | $CHNO_2$ | |
| 3-1.30 | cyclohexyl | H | $NHCH_3$ | $N-NO_2$ | |
| 3-1.31 | cyctohexyl | H | $NHC_2H_5$ | $N-NO_2$ | |
| 3-1.32 | cyctohexyl | $CH_3$ | $NHCH_3$ | $N-NO_2$ | |
| 3-1.33 | cyclohexyl | $CH_3$ | $N(CH_3)$ | $N-NO_2$ | |
| 3-1.34 | cyclohexyl | $CH_3$ | $NHC_2H_5$ | $N-CN$ | |
| 3-1.35 | cyclohexyl | $C_2H_5$ | $NHCH_2$ | $N-CN$ | |
| 3-1.36 | $CH_2=CH-CH_2-$ | $CH_3$ | $N(CH_3)_2$ | $CHNO_2$ | |
| 3-1.37 | $CH_2=CH-CH_2-$ | $CH_3$ | $NHCH_3$ | $CHNO_2$ | |
| 3-1.38 | $CH_2=CH-CH_2-$ | H | $N(CH_3)_2$ | $CHNO_2$ | |
| 3-1.39 | $ClCH=CH-CH_2-$ | H | $NHC_2H_5$ | $CHNO_2$ | |
| 3-1.40 | $ClCH=CH-CH_2-$ | H | $NHCH_3$ | $N-NO_2$ | |
| 3-1.41 | $ClCH=CH-CH_2-$ | H | H | $N-NO_2$ | |

TABLE 3-1-continued

Compounds of the formula

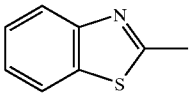

| Comp. No. | R | $R_1$ | $Z-R_2$ | Q-Y | M.p. (° C.) |
|---|---|---|---|---|---|
| 3-1.42 | $CH_2=C(CH_3)-CH_2-$ | $CH_3$ | $NH_2$ | $N-NO2$ | |
| 3-1.43 | $CH_2=CH-(CH_2)_2-$ | $CH_3$ | $NHC_2H_5$ | $N-NO_2$ | |
| 3-1.44 | 2-chlorobenzyl | $CH_3$ | $NHCH_3$ | $N-NO_2$ | |
| 3-1.45 | 4-chlorobenzyl | $C_2H_5$ | $NHCH_3$ | $N-NO_2$ | |
| 3-1.46 | $CH\equiv C-CH_2-$ | $CH_3$ | $N(CH_3)_2$ | $N-NO_2$ | |
| 3-1.47 | isopropyl | $CH_3$ | $NHCH_3$ | $N-CN$ | |
| 3-1.48 | $C_2H_5-OC(=O)-CH_2-$ | H | $N(CH_3)_2$ | $N-CN$ | |
| 3-1.49 | 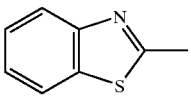 | H | $NHC_2H_5$ | $CHNO_2$ | |
| 3-1.50 | $n-C_3H_7-$ | H | $NHCH_3$ | $CHNO_2$ | |
| 3-1.51 | $HO-CH_2-CH_2-$ | H | H | $CHNO_2$ | |
| 3-1.52 | tert-butyl | $CH_3$ | $NH_2$ | $CHNO_2$ | |
| 3-1.53 | $n-C_{12}H_{25}-$ | $CH_3$ | $NHC_2H_5$ | $N-NO_2$ | |
| 3-1.54 | tert-butyl | $CH_3$ | $NHCH_3$ | $N-NO_2$ | |
| 3-1.55 | $n-C_{12}H_{25}-$ | H | $NH_2$ | $N-CN$ | |
| 3-1.56 | tert-butyl | $CH_3$ | $NH_2$ | $N-CN$ | |
| 3-1.57 | $n-C_{12}H_{25}-$ | $C_2H_5$ | $NH_2$ | $CHNO_2$ | |
| 3-1.58 | 2-ethyl-pentyl | $C_2H_5$ | $NHCH_3$ | $CHNO_2$ | |
| 3-1.59 | 2-ethyl-pentyl | H | $NHCH_3$ | $CHNO_2$ | |
| 3-1.60 | benzyl | H | $NHC_2H_5$ | $CHNO_2$ | |
| 3-1.61 | phenyl | $CH_3$ | $NHCH_3$ | $N-NO_2$ | |
| 3-1.62 | cyclohexyl | $CH_3$ | $N(CH_3)_2$ | $N-CN$ | |
| 3-1.63 | $CH_2=CH-CH_2-$ | H | $NH_2$ | $N-CN$ | |
| 3-1.64 | $CH_2=CH-CH_2-$ | $CH_3$ | $NH_2$ | $CHNO_2$ | |
| 3-1.65 | $ClCH=CH-CH_2-$ | H | $NH_2$ | $CHNO_2$ | |
| 3-1.66 | $CH_2=C(CH_3)-CH_2-$ | $CH_3$ | $NH_2$ | $CHNO_2$ | |
| 3-1.67 | $CH_2=CH-CH_2-CH_2-$ | $C_2H_5$ | $NH_2$ | $CHNO_2$ | |
| 3-1.68 | 2-chlorobenzyl | $C_2H_5$ | $NHCH_3$ | $N-NO_2$ | |
| 3-1.69 | 4-chlorobenzyl | H | $NHCH_3$ | $N-NO_2$ | |
| 3-1.70 | $CH\equiv C-CH_2-$ | H | $NHC_2H_5$ | $N-CN$ | |
| 3-1.71 | isopropyl | $CH_3$ | $NHCH_3$ | $CHNO_2$ | |
| 3-1.72 | $C_2H_5-OC(=O)-CH_2-$ | $CH_3$ | $N(CH_3)_2$ | $CHNO_2$ | |
| 3.173 | 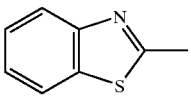 | H | $NH_2$ | $CHNO_2$ | |
| 3-1.74 | $n-C_3H_7-$ | $CH_3$ | $NH_2$ | $CHNO_2$ | |
| 3-1.75 | $HO-CH_2-CH_2-$ | $CH_3$ | $NH_2$ | $N-NO_2$ | |
| 3-1.76 | tert-butyl | $C_2H_5$ | $NH_2$ | $N-CN$ | |
| 3-1.77 | $n-C_{12}H_{25}-$ | $C_2H_5$ | $NHCH_3$ | $CHNO_2$ | |
| 3-1.78 | 2-ethylpentyl | H | $NHCH_3$ | $N-NO_2$ | |

TABLE 3-2

Compounds of the formula

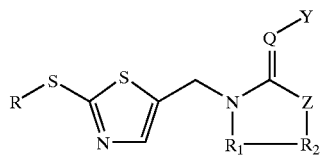

| No. | R | R₁ R₂ | Z | Q-Y | M.p. |
|---|---|---|---|---|---|
| 3-2.1 | benzyl | —CH₂—O—CH₂— | NH | N—NO₂ | amorphous |
| 3-2.2 | phenyl | —CH₂—O—CH₂— | NH | N—NO₂ | |
| 3-2.3 | phenyl | —CH₂—O—CH₂— | N—CH₃ | N—NO₂ | 147° C. |
| 3-2.4 | 4-CH₃-phenyl | —CH₂—O—CH₂— | N—CH₃ | N—NO₂ | 160–162° C. |
| 3-2.5 | CH₃ | —CH₂—O—CH₂— | N—CH₃ | N—NO₂ | 135–137° C. |
| 3-2.6 | phenyl | —CH₂—O—CH₂— | N—C₂H₅ | N—NO₂ | |
| 3-2.7 | phenyl | —CH₂—O—CH₂— | N—C₃H₇ | N—NO₂ | |
| 3-2.8 | benzyl | —CH₂—O—CH₂— | N—CH₃ | N—NO₂ | 140–145° C. |
| 3-2.9 | cyclohexyl | —CH₂—O—CH₂— | NH | N—NO₂ | |
| 3-2.10 | cyclohexyl | —CH₂—O—CH₂— | N—CH₃ | N—NO₂ | 109–110° C. |
| 3-2.11 | cyclohexyl | —CH₂—O—CH₂— | N—C₂H₅ | N—NO₂ | |
| 3-2.12 | cyclohexyl | —CH₂—O—CH₂— | N-C₃H₇ | N—NO₂ | |
| 3-2.13 | benzyl | —CH₂—O—CH₂— | N-n-C₄H₉ | N—NO₂ | amorphous |
| 3-2.14 | phenyl | —CH₂—O—CH₂— | N-n-C₄H₉ | N—NO₂ | |
| 3-2.15 | benzyl | —CH₂—O—CH₂— | N—CH₂—CH=CH₂ | N—NO₂ | |
| 3-2.16 | benzyl | —CH₂—O—CH₂— | N—CH₂—C≡CH | N—NO₂ | solid |
| 3-2.17 | benzyl | —CH₂—N(CH₃)—CH₂— | NH | N—NO₂ | |
| 3-2.18 | benzyl | —CH₂—N(CH₃)—CH₂— | N—CH₃ | N—NO₂ | |
| 3-2.19 | benzyl | —CH₂—N(CH₂—CH₃)—CH₂— | NH | N—NO₂ | |
| 3-2.20 | phenyl | —CH₂—N(CH₂—CH₃)—CH₂— | NH | N—NO₂ | |
| 3-2.21 | benzyl | —CH₂—N(CH₂—CH₃)—CH₂— | N—CH₃ | N—NO₂ | |
| 3-2.22 | phenyl | —CH₂—N(n-C₃H₇)—CH₂— | NH | N—NO₂ | |
| 3-2.23 | phenyl | —CH₂—N(n-C₃H₇)—CH₂— | N—CH₃ | N—NO₂ | |
| 3-2.24 | phenyl | —CH₂—N(CH₂—CH(CH₃)₂)—CH₂— | NH | N—NO₂ | |
| 3-2.25 | benzyl | —CH₂—N(CH₂—CH(CH₃)₂)—CH₂— | N—CH₃ | N—NO₂ | |
| 3-2.26 | benzyl | —CH₂—CH₂—CH₂— | NH | N—NO₂ | amorphous |
| 3-2.27 | benzyl | —CH₂—CH₂—CH₂— | N—CH₃ | N—NO₂ | |
| 3-2.28 | benzyl | —CH₂—CH₂— | NH | N—NO₂ | solid |
| 3-2.29 | benzyl | —CH₂—CH₂— | N—CH₃ | N—NO₂ | amorphous |
| 3-2.30 | phenyl | —CH₂—CH₂—CH₂— | S | N—NO₂ | |
| 3-2.31 | phenyl | —CH₂—CH₂— | S | N—NO₂ | |
| 3-2.32 | phenyl | —CH₂—O—CH₂— | NH | N—CN | |
| 3-2.33 | phenyl | —CH₂—O—CH₂— | NH | N—CN | |
| 3-2.34 | benzyl | —CH₂—O—CH₂— | N—CH₃ | N—CN | |
| 3-2.35 | benzyl | —CH₂—O—CH₂— | N—CH₂—CH₃ | N—CN | |
| 3-2.36 | benzyl | —CH₂—O—CH₂— | N-n-C₃H₇ | N—CN | |
| 3-2.37 | benzyl | —CH₂—O—CH₂— | N-n-C₄H₉ | N—CN | |
| 3-2.38 | benzyl | —CH₂—O—CH₂— | NCH₂CH=CH₂ | N—CN | |
| 3-2.39 | benzyl | —CH₂—O—CH₂— | N—CH₂≡CH | N—CN | |
| 3-2.40 | phenyl | —CH₂—N(CH₃)—CH₂— | NH | N—CN | |
| 3-2.41 | phenyl | —CH₂—N(CH₃)—CH₂— | N—CH₃ | N—CN | |
| 3-2.42 | phenyl | —CH₂—N(CH₂—CH₃)—CH₂— | NH | N—CN | |
| 3-2.43 | phenyl | —CH₂—N(CH₂—CH₃)—CH₂— | N—CH₃ | N—CN | |
| 3-2.44 | phenyl | —CH₂—N(n-C₃H₇)—CH₂— | NH | N—CN | |
| 3-2.45 | phenyl | —CH₂—N(n-C₃H₇)—CH₂— | N—CH₃ | N—CN | |
| 3-2.46 | benzyl | —CH₂—N(CH₂—CH(CH₃)₂)—CH₂— | NH | N—CN | |
| 3-2.47 | benzyl | —CH₂—N(CH₂—CH(CH₃)₂)—CH₂— | N—CH₃ | N—CN | |
| 3-2.48 | benzyl | —CH₂—CH₂—CH₂— | NH | N—CN | amorphous |
| 3-2.49 | phenyl | —CH₂—CH₂—CH₂— | N—CH₃ | N—CN | solid |
| 3-2.50 | phenyl | —CH₂—CH₂— | NH | N—CN | |
| 3-2.51 | benzyl | —CH₂—CH₂— | N—CH₃ | N—CN | |
| 3-2.52 | benzyl | —CH₂—CH₂—CH₂— | S | N—CN | |
| 3-2.53 | benzyl | —CH₂—CH₂— | S | N—CN | |
| 3-2.54 | phenyl | —CH₂—CH₂—CH₂— | CH | N—NO₂ | |
| 3-2.55 | phenyl | —CH₂—CH₂— | C—CH₃ | N—NO₂ | |
| 3-2.56 | phenyl | —CH₂—O—CH₂— | C—C₂H₅ | N—NO₂ | |
| 3-2.57 | isopropyl | —CH₂—CH₂— | NH | N—NO₂ | |
| 3-2.58 | C₂H₅—OC(=O)—CH₂— | —CH₂—O—CH₂— | NH | N—NO₂ | |

TABLE 3-2-continued

Compounds of the formula

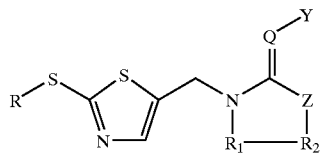

| No. | R | $R_1$ $R_2$ | Z | Q-Y | M.p. |
|---|---|---|---|---|---|
| 3-.259 | benzothiazol-2-yl | —CH$_2$—CH$_2$— | NH | N—NO$_2$ | |
| 3-2.60 | n-C$_3$H$_7$— | —CH$_2$—O—CH$_2$— | NH | N—NO$_2$ | |
| 3-2.61 | n-C$_3$H$_7$— | —CH$_2$—O—CH$_2$— | NCH$_3$ | N—NO$_2$ | 67–72° C. |
| 3-2.62 | HO—CH$_2$—CH$_2$— | —CH$_2$—CH$_2$— | NH | N—NO$_2$ | |
| 3-2.63 | tert-butyl | —CH$_2$—O—CH$_2$— | N—CH$_3$ | N—NO$_2$ | |
| 3-2.64 | n-C$_{12}$H$_{25}$— | —CH$_2$—CH$_2$— | N—CH$_3$ | N—NO$_2$ | |
| 3-2.65 | tert-butyl | —CH$_2$—O—CH$_2$— | NH | N—NO$_2$ | |
| 3-2.66 | n-C$_{12}$H$_{25}$— | —CH$_2$—CH$_2$— | N—CH$_3$ | N—NO$_2$ | |
| 3-2.67 | tert-butyl | —CH$_2$—O—CH$_2$— | NH | N—NO$_2$ | |
| 3-2.68 | n-C$_{12}$H$_{25}$— | —CH$_2$—CH$_2$— | N—CH$_3$ | N—NO$_2$ | |
| 3-2.69 | 2-ethyl-pentyl | —CH$_2$—O—CH$_2$— | NH | N—NO$_2$ | |
| 3-2.70 | 2-ethyl-pentyl | —CH$_2$—CH$_2$— | N—CH$_3$ | N—NO$_2$ | |
| 3-2.71 | cyclohexyl | —CH$_2$—O—CH$_2$— | N—C$_2$H$_5$ | N—NO$_2$ | |
| 3-2.72 | CH$_2$=CH—CH$_2$— | —CH$_2$—CH$_2$— | NH | N—NO$_2$ | |
| 3-2.73 | CH$_2$=CH—CH$_2$— | —CH$_2$—O—CH$_2$— | N—CH$_3$ | N—NO$_2$ | |
| 3-2.74 | ClCH=CH—CH$_2$— | —CH$_2$—CH$_2$— | N—C$_2$H$_5$ | N—NO$_2$ | |
| 3-2.75 | CH$_2$=C(CH$_3$)—CH$_2$— | —CH$_2$—O—CH$_2$— | N—CH$_3$ | N—NO$_2$ | |
| 3-2.76 | CH$_2$=CH—CH$_2$—CH$_2$— | —CH$_2$—CH$_2$— | NH | N—NO$_2$ | |
| 3-2.77 | 2-chlorobenzyl | —CH$_2$—O—CH$_2$— | N—CH$_3$ | N—NO$_2$ | |
| 3-2.78 | 4-chlorobenzyl | —CH$_2$—CH$_2$— | NH | N—NO$_2$ | |
| 3-2.79 | CH≡C—CH$_2$— | —CH$_2$—O—CH$_2$— | N—CH$_3$ | N—NO$_2$ | |
| 3-2.80 | HS—(CH$_2$)$_5$— | —CH$_2$—O—CH$_2$— | N—C$_3$H$_7$ | N—NO$_2$ | |
| 3-2.81 | HS—(CH$_2$)$_5$— | CH$_2$—CH$_2$—CH$_2$— | N—C$_3$H$_7$ | N—NO$_2$ | |
| 3-2.82 | HS—(CH$_2$)$_5$— | —CH$_2$—CH$_2$— | N—C$_3$H$_7$ | N—NO$_2$ | |
| 3-2.83 | —CH$_2$—C$_6$H$_4$-4-CH$_2$—SH | —CH$_2$—O—CH$_2$— | N—C$_3$H$_7$ | N—NO$_2$ | |
| 3-2.84 | —CH$_2$—C$_6$H$_4$-4-CH$_2$—SH | CH$_2$—CH$_2$—CH$_2$— | N—C$_3$H$_7$ | N—NO$_2$ | |
| 3-2.85 | —CH$_2$—C$_6$H$_4$-4-CH$_2$—SH | —CH$_2$—CH$_2$— | N—C$_3$H$_7$ | N—NO$_2$ | |
| 3-2.86 | HS—(CH$_2$)$_5$— | —CH$_2$—O—CH$_2$— | N—CH$_3$ | N—NO$_2$ | 57–60° C. |
| 3-2.87 | HS—(CH$_2$)$_5$— | —CH$_2$—CH$_2$—CH$_2$— | N—CH$_3$ | N—NO$_2$ | |
| 3-2.88 | HS—(CH$_2$)$_5$— | —CH$_2$—CH$_2$— | N—CH$_3$ | N—NO$_2$ | |
| 3-2.89 | —CH$_2$—C$_6$H$_4$-4-CH$_2$—SH | —CH$_2$—O—CH$_2$— | N—CH$_3$ | N—NO$_2$ | 110–112° C. |
| 3-2.90 | —CH$_2$—C$_6$H$_4$-4-CH$_2$—SH | —CH$_2$—CH$_2$—CH$_2$— | N—CH$_3$ | N—NO$_2$ | |
| 3-2.91 | —CH$_2$—C$_6$H$_4$-4-CH$_2$—SH | —CH$_2$—CH$_2$— | N—CH$_3$ | N—NO$_2$ | |

Example P4
3-(2-Chloro-thiazol-5-yl-methyl)-5-methyl-4-nitroimino-perhydro-1,3,5-oxadiazine (compound 4-2)

a) 183 g of 3-(2-phenylthio-thiazol-5-yl-methyl)-5-methyl-4-nitroimino-perhydro-1,3,5-oxadiazine are introduced over a period of 5 minutes, with stirring, into a mixture of 300 g of hydrochloric acid (32%) and 150 g of chlorobenzene. 124 g of chlorine are introduced at 20° C. over a period of 4 hours. After 2 hours, excess chlorine is removed by the introduction of nitrogen, and the phases are then separated. The aqueous phase is adjusted to pH 5 with sodium hydroxide solution (30%) and then filtered, and the filtration residue is washed with water and dried in vacuo at 50° C. The title product is obtained in a purity of 97%.

b) 186 g of 3-(2cyclohexylthio-thiazol-5-yl-methyl)-5-methyl-4-nitroimino-perhydro-1,3,5-oxadiazine are introduced over a period of 5 minutes, with stirring, into a mixture of 300 g of hydrochloric acid (32%) and 150 g of chlorobenzene. 124 g of chlorine are introduced at 20° C. over a period of 4 hours. After 2 hours, excess chlorine is removed by the introduction of nitrogen, and the phases are then separated. The aqueous phase is adjusted to pH 5 with sodium hydroxide solution (30%) and then filtered, and the filtration residue is washed with water and dried in vacuo at 50° C. The title product is obtained in a purity of 97%.

c) 190 g of 3-(2-benzylthio-thiazol-5-yl-methyl)-5-methyl-4-nitroimino-perhydro-1,3,5-oxadiazine are introduced over a period of 5 minutes, with stirring, into a mixture of 300 g of hydrochloric acid (32%) and 150 g of chlorobenzene. 124 g of chlorine are introduced at 20° C. over a period of 4 hours. After 2 hours, excess chlorine is removed by the introduction of nitrogen, and the phases are then separated. The aqueous phase is adjusted to pH 5 with sodium hydroxide solution (30%) and then filtered, and the filtration residue is washed with water and dried in vacuo at 50° C. The title product is obtained in a purity of 97%.

Example P4d

The other compounds listed in Tables 4-1 and 4-2 can also be prepared in a manner analogous to that described in Examples P4a to P4c.

TABLE 4

Compounds of the formula

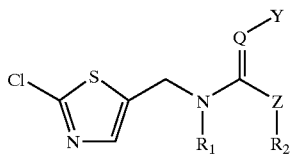

| No. | R₁ | R₂ | Z | Q-Y | M.p.(° C.) |
|---|---|---|---|---|---|
| 4-1 | —CH₂—O—CH₂— | | NH | N—NO₂ | 146° C. |
| 4-2 | —CH₂—O—CH₂— | | N—CH₃ | N—NO₂ | 138–140° C. |
| 4-3 | —CH₂—O—CH₂— | | N—CH₂—CH₃ | N—NO₂ | |
| 4-4 | —CH₂—O—CH₂— | | N—CH₂—CH₂—CH₃ | N—NO₂ | |
| 4-5 | —CH₂—O—CH₂— | | N-n-C₄H₉ | N—NO₂ | 73° C. |
| 4-6 | —CH₂—O—CH₂— | | N—CH₂—CH=CH₂ | N—NO₂ | |
| 4-7 | —CH₂—O—CH₂— | | N—CH₂—C≡CH | N—NO₂ | 176° C. |
| 4-8 | —CH₂—N(CH₃)—CH₂— | | NH | N—NO₂ | |
| 4-9 | —CH₂—N(CH₃)—CH₂— | | N—CH₃ | N—NO₂ | |
| 4-10 | —CH₂—N(CH₂—CH₃)—CH₂— | | NH | N—NO₂ | |
| 4-11 | —CH₂—N(CH₂—CH₃)—CH₂— | | N—CH₃ | N—NO₂ | |
| 4-12 | —CH₂—N(n-C₃H₇)—CH₂— | | NH | N—NO₂ | |
| 4-13 | —CH₂—N(n-C₃H₇)—CH₂— | | N—CH₃ | N—NO₂ | |
| 4-14 | —CH₂—N(CH₂—CH(CH₃)₂)—CH₂— | | NH | N—NO₂ | |
| 4-15 | —CH₂—N(CH₂—CH(CH₃)₂)—CH₂— | | N—CH₃ | N—NO₂ | |
| 4-16 | —CH₂—CH₂—CH₂— | | NH | N—NO₂ | 125° C. |
| 4-17 | —CH₂—CH₂—CH₂— | | N—CH₃ | N—NO₂ | |
| 4-18 | —CH₂—CH₂— | | NH | N—NO₂ | 150° C. |
| 4-19 | —CH₂—CH₂— | | N—CH₃ | N—NO₂ | 112° C. |
| 4-20 | H | CH₃ | NH | N—NO₂ | |
| 4-21 | CH₃ | H | NH | N—NO₂ | |
| 4-22 | H | H | NH | N—NO₂ | |
| 4-23 | CH₃ | CH₃ | NH | N—NO₂ | |
| 4-24 | H | CH₃ | N—CH₃ | N—NO₂ | |
| 4-25 | CH₃ | CH₃ | N—CH₃ | N—NO₂ | |
| 4-26 | —CH₂—CH₂—CH₂— | | S | N—NO₂ | |
| 4-27 | —CH₂—CH₂— | | S | N—NO₂ | |
| 4-28 | —CH₂—O—CH₂— | | NH | N—CN | |
| 4-29 | —CH₂—O—CH₂— | | N—CH₃ | N—CN | |
| 4-30 | —CH₂—O—CH₂— | | N—CH₂—CH₃ | N—CN | |
| 4-31 | —CH₂—O—CH₂— | | N—CH₂—CH₂—CH₃ | N—CN | |
| 4-32 | —CH₂—O—CH₂— | | N-n-C₄H₉ | N—CN | |
| 4-33 | —CH₂—O—CH₂— | | N—CH₂—CH=CH₂ | N—CN | |
| 4-34 | —CH₂—O—CH₂— | | N—CH₂—C≡CH | N—CN | |
| 4-35 | —CH₂—N(CH₃)—CH₂— | | NH | N—CN | |
| 4-36 | —CH₂—N(CH₃)—CH₂— | | N—CH₃ | N—CN | |
| 4-37 | —CH₂—N(CH₂—CH₃)—CH₂— | | NH | N—CN | |
| 4-38 | —CH₂—N(CH₂—CH₃)—CH₂— | | N—CH₃ | N—CN | |
| 4-39 | —CH₂—N(n-C₃H₇)—CH₂— | | NH | N—CN | |
| 4-40 | —CH₂—N(n-C₃H₇)—CH₂— | | N—CH₃ | N—CN | |
| 4-41 | —CH₂—N(CH₂—CH(CH₃)₂)—CH₂— | | NH | N—CN | |
| 4-42 | —CH₂—N(CH₂—CH(CH₃)₂)—CH₂— | | N—CH₃ | N—CN | |
| 4-43 | —CH₂—CH₂—CH₂— | | NH | N—CN | 176° C. |
| 4-44 | —CH₂—CH₂—CH₂— | | N—CH₃ | N—CN | solid |
| 4-45 | —CH₂—CH₂— | | NH | N—CN | |
| 4-46 | —CH₂—CH₂— | | N—CH₃ | N—CN | |
| 4-47 | H | CH₃ | N—CN | N—CN | |
| 4-48 | CH₃ | H | NH | N—CN | |
| 4-49 | H | H | NH | N—CN | |
| 4-50 | CH₃ | CH₃ | NH | N—CN | |
| 4-51 | H | CH₃ | N—CH₃ | N—CN | |
| 4-52 | CH₃ | CH₃ | N—CH₃ | N—CN | |
| 4-53 | —CH₂—CH₂—CH₂— | | S | N—CN | |
| 4-54 | —CH₂—CH₂— | | S | N—CN | |

What is claimed is:

1. A process for the preparation of a compound of the formula

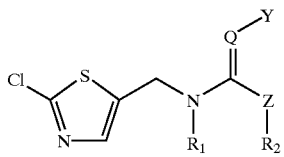
(I)

wherein
R is as defined for the formula (II);
m is 0 or 1; and
X is halogen; which comprises reacting a compound of the formula

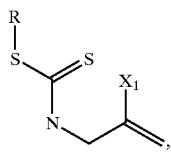
(II)

in free form or salt form, wherein

R is unsubstituted or substituted $C_1$–$C_{12}$alkyl, unsubstituted or substituted $C_2$–$C_4$alkenyl, unsubstituted or substituted $C_2$–$C_4$alkynyl, unsubstituted or substituted $C_3$–$C_6$-cycloalkyl, unsubstituted or substituted aryl, unsubstituted or substituted heterocyclyl being a five- to seven-membered monocyclic saturated or unsaturated moiety, that contains from one to three hetero atoms selected from the group consisting of N, O and S, or a bicyclic moiety that may contain either in one ring or in both rings one or more hetero atoms selected from the group consisting of N, O and S, or —$SR_6$;

$R_6$ is unsubstituted or substituted $C_1$–$C_{12}$alkyl, unsubstituted or substituted $C_2$–$C_4$alkenyl, unsubstituted or substituted $C_2$–$C_4$alkynyl, unsubstituted or substituted $C_3$–$C_6$cycloalkyl, unsubstituted or substituted aryl or unsubstituted or substituted heterocyclyl being a five- to seven-membered monocyclic saturated or unsaturated moiety, that contains from one to three hetero atoms selected from the group consisting of N, O and S, or a bicyclic moiety that may contain either in one ring or in both rings one or more hetero atoms selected from the group consisting of N, O and S; and $X_1$ is a leaving group;
with a halogenating agent.

* * * * *